(12) United States Patent
Brandenburg et al.

(10) Patent No.: US 10,980,908 B1
(45) Date of Patent: Apr. 20, 2021

(54) FRAGRANCE SACHET WITH MULTIPLE ATTACHMENT CONFIGURATIONS

(71) Applicant: Brandywine Product Group International, Inc., Wilmington, DE (US)

(72) Inventors: Kyle Brandenburg, Middletown, DE (US); Kimberly Gobel, Kennett Square, PA (US)

(73) Assignee: Brandywine Product Group International, Inc., Wilmington, DE (US)

(*) Notice: Subject to any disclaimer, the term of this patent is extended or adjusted under 35 U.S.C. 154(b) by 81 days.

(21) Appl. No.: 16/059,102

(22) Filed: Aug. 9, 2018

(51) Int. Cl.
*A61L 9/12* (2006.01)

(52) U.S. Cl.
CPC ............. *A61L 9/12* (2013.01); *A61L 2209/15* (2013.01)

(58) Field of Classification Search
CPC ........ A61L 9/125; A61L 9/12; A61L 2209/15; A44B 17/00; A01M 31/008; A01M 1/2055; Y10T 24/1397
USPC ...................................................... 239/34–60
See application file for complete search history.

(56) References Cited

U.S. PATENT DOCUMENTS

| | | | |
|---|---|---|---|
| 1,898,621 A * | 2/1933 | Ferguson | A01M 1/2055 239/57 |
| 2,615,754 A * | 10/1952 | Lindenberg | A45D 37/00 239/36 |
| 3,087,679 A * | 4/1963 | Wilson | A01M 1/205 239/57 |
| 3,521,816 A * | 7/1970 | Wilson | A01M 1/2055 239/60 |
| 4,854,501 A | 8/1989 | Ricci | |
| 5,383,598 A * | 1/1995 | Styles | A61L 9/12 239/34 |
| 5,823,432 A * | 10/1998 | Hogan | A61L 9/12 239/36 |
| 6,213,409 B1 | 4/2001 | Warren | |
| 6,613,287 B1 * | 9/2003 | McElligott | A61L 9/042 239/57 |
| 6,736,335 B2 | 5/2004 | Cuthbert | |
| 6,857,579 B2 | 2/2005 | Harris | |
| 9,623,136 B2 * | 4/2017 | Dobler | A61L 9/12 |
| 2003/0064009 A1 * | 4/2003 | Baaset | A45C 13/00 422/123 |
| 2006/0168766 A1 * | 8/2006 | Lippincott | A61J 17/111 24/3.13 |
| 2007/0140923 A1 * | 6/2007 | Wiegand | A01M 1/2055 422/124 |
| 2008/0105760 A1 * | 5/2008 | Sheffield | A61L 9/04 239/56 |

(Continued)

*Primary Examiner* — Joseph A Greenlund
(74) *Attorney, Agent, or Firm* — Rogowski Law LLC

(57) ABSTRACT

A pouch filled with a fragrance material has a proximal end of a strap joined thereto. A first fastener is appended on a rear face of the strap, at or near the proximal end. A second fastener is appended on the rear face of the strap at or near the distal end of the strap. Preferably, a third fastener is on or appended to a rear face of the pouch. The second fastener, such as a male snap fastener, is removably joinable to either the first fastener to form a loop in the strap or to the third fastener so that the rear face of the strap faces the rear face of the pouch. The pouch may be suspended from a mounting structure, such as a neck of a rear-view mirror of an automobile, by the strap in either configuration.

15 Claims, 7 Drawing Sheets

(56) References Cited

U.S. PATENT DOCUMENTS

| | | | | |
|---|---|---|---|---|
| 2009/0302128 A1* | 12/2009 | Zobele | ............. | A61L 9/12 |
| | | | | 239/59 |
| 2010/0308131 A1* | 12/2010 | Hogan | ............. | A61L 9/042 |
| | | | | 239/36 |
| 2013/0253257 A1* | 9/2013 | Kalhory | ............. | A61F 7/02 |
| | | | | 600/27 |
| 2014/0367484 A1* | 12/2014 | Kramer | ............. | A61L 9/12 |
| | | | | 239/44 |
| 2018/0099065 A1* | 4/2018 | Burns | ............. | A61L 9/044 |

* cited by examiner

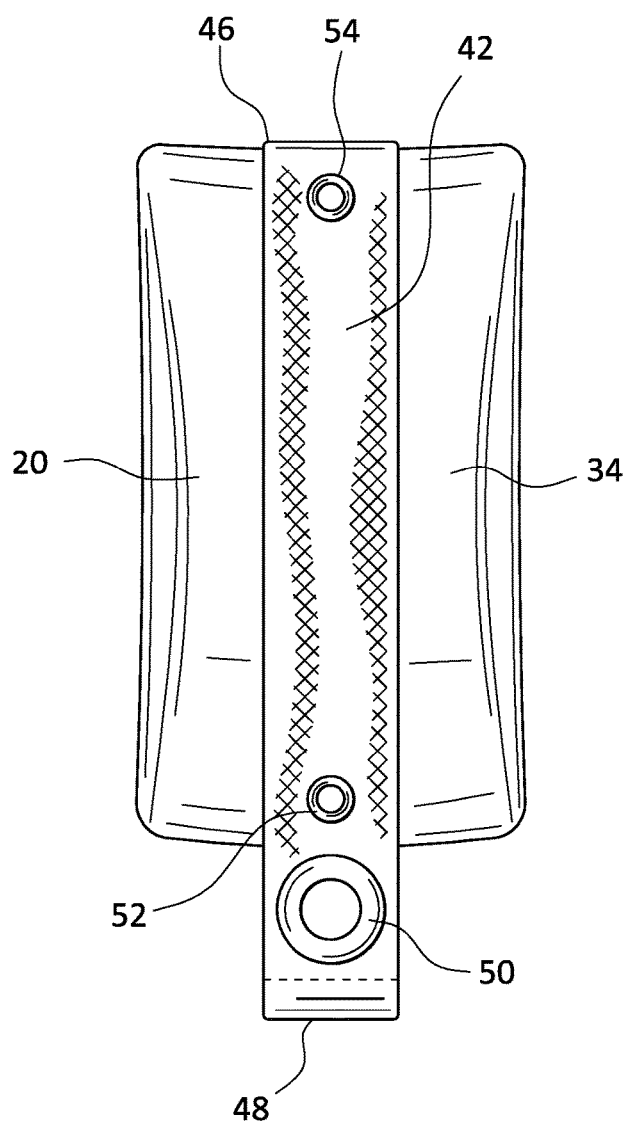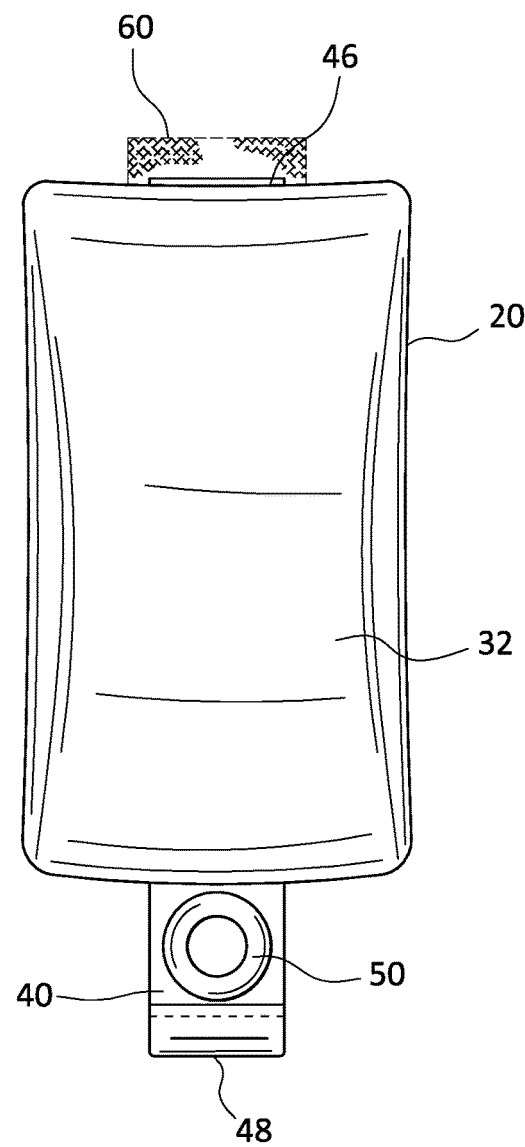

FRAGRANCE SACHET WITH MULTIPLE ATTACHMENT CONFIGURATIONS

BACKGROUND OF THE INVENTION

The present invention is generally directed to a pouch filled with a volatile material that has a strap joined thereto from which the pouch may be suspended, wherein the strap has a fastener at its distal end that may be engaged either to a mating fastener on the strap to form a hanging loop, or, optionally, to a mating fastener on a face surface of the pouch to form a hanging handle.

The passenger compartments of automobiles and trucks may retain unpleasant odors introduced into such compartment by drivers, passengers or cargo. Examples of unpleasant odors include cigarette and cigar smoke, food odors, body odors, retained cargo odors and gas or exhaust fumes. Various air freshener devices have been designed for use in vehicle passenger compartments, including devices that suspend from a rear-view mirror or from a sun visor.

Effective continuous action air fresheners release a sufficient amount of fragrance such that for a given enclosed space, such as a room or a motor vehicle passenger compartment, the fragrance is readily perceptible when someone enters that space.

Air freshening clips that join to the fins of automotive or household venting systems are shown in the prior art. See, e.g., U.S. Pat. Nos. 5,407,642; 5,527,493; 5,865,372; 6,264,887; and 7,687,038. Other representative hanging or suspending air freshener devices include charms or novelty devices hung by string or stretchable elastic yarns, or air freshening devices suspended by hooks. See, e.g., U.S. Pat. Nos. 7,182,270 and 5,468,447. Scent emitting clothes hangers are also known. See, e.g., U.S. Pat. No. 6,149,038.

Consumers may prefer portable air freshener devices that may be installed quickly and removed quickly from living spaces and motor vehicle passenger compartments. Devices that may be moved from one location to another location easily also are preferred. Consumers further may prefer air freshener devices with outer configurations that more discretely fit within a living space or motor vehicle passenger compartment. One novel air freshener meeting these criteria is a rounded clip shown in U.S. Pat. No. 9,107,969.

Improvements to air freshener devices for use in conjunction with small spaces, such as motor vehicle passenger compartments, closets and storage areas, continue to be sought. Most desirably, air freshener devices will emit a desired level of fragrance or volatile into the air without harming furniture or automotive interior surfaces.

BRIEF SUMMARY OF THE INVENTION

Briefly stated, one aspect of the present invention is a fragrance sachet formed of a pouch configured to receive a volatile material. The pouch may be filled with a stuffing material or flowable particulate that is impregnated with the volatile material. The pouch may be made of a fabric, such as knit, woven or nonwoven, and may be cotton, polyester or a cotton/polyester blend. The pouch has a front face and a rear face opposite the front face.

A strap is joined to the pouch. The strap has a proximal end and a distal end, and a length between the proximal end and the distal end, and has a front face and a rear face opposite the front face. The proximal end of the strap is joined to the pouch. The strap may be made of a fabric, such as cotton, polyester or a cotton/polyester blend. Alternatively, the strap may be an elastic band, such as a braided elastic band.

Two fasteners are present on the rear face of the strap. One fastener (e.g., the first fastener of the fragrance sachet) is positioned at or near the proximal end of the strap. Another fastener (e.g., the second fastener of the fragrance sachet) is positioned at a location along the length of the strap, spaced apart from the other fastener on the rear face of the strap. The second fastener is adapted for mating connection to the first fastener on the strap. When the second fastener is joined to first fastener (on the strap), the strap forms a loop from which the pouch may be suspended.

Optionally, a third fastener, such as a snap fastener or a VELCRO® brand hook/loop fastener patch, is on or appended to the rear face of the pouch. When the third fastener is present, the second fastener is adapted for mating connection to either the third fastener on the rear side of the pouch or the first fastener on the strap. When the second fastener is joined to the third fastener (on the rear face of the pouch), the strap lays across a portion of the rear face of the pouch, and the pouch may be suspended from the strap.

In a preferred embodiment, the second fastener comprises a male snap, and the first and third fasteners comprise female snaps adapted to removably receive the male snap.

In one variant, a hole is formed through the strap at or near the distal end of the strap. The hole may be reinforced by a grommet. In this variant, the pouch may be suspended from the strap, with the hole joining to a mounting.

In a preferred embodiment, the front face of the pouch is free of all fasteners. In such an embodiment, the front face of the pouch may display indicia or artwork, such as advertising material or logos. Alternatively, indicia or artwork may be applied to a surface of the strap.

The volatile material may be any fragrance material that emits desired fragrance, such as natural and synthetic fragrance oils, and mixtures thereof. In one embodiment, the fragrance sachet comprises a pouch and a stuffing material held within the pouch, wherein said stuffing material is impregnated with the volatile material.

Also contemplated within the scope of the invention is a method for suspending a fragrance sachet to a support structure. By support structure is meant any structure within a living space or a motor vehicle passenger compartment from which a fragrance sachet may be suspended. One exemplary support structure is a neck of a rear-view mirror of a motor vehicle.

In the method, a pouch configured to receive a volatile material is provided. The pouch has a front face and a rear face opposite the front face, with a strap joined to the pouch, the strap having a proximal end and a distal end, and a length between the proximal end and the distal end, wherein the proximal end is joined to the pouch, the strap having a front face and a rear face opposite the front face, and a first fastener at or near the proximal end of the strap, and a second fastener positioned at a location along the length of the strap, spaced apart from the first fastener.

Optionally, a third fastener is on or appended to the rear face of the pouch.

The pouch filled with volatile material or stuffing material impregnated with volatile material is placed so that its rear face is near a mounting portion of the support structure. The strap is wrapped over the mounting portion of the support structure. The second fastener is engaged to the first fastener to form a loop in the strap from which the pouch may be suspended. If the optional third fastener is present, the second fastener may alternatively be engaged with the third fastener. In one embodiment, the first fastener and third fastener are female snap fasteners, and the second snap fastener is a male snap fastener. When suspended from the support structure with the second fastener joined to the third fastener, the rear face of the pouch faces the mounting structure. When the second fastener is fastened to the first fastener, a loop is formed in the strap, and the pouch is suspended from the support structure by the loop.

BRIEF DESCRIPTION OF THE DRAWINGS

The foregoing summary, as well as the following detailed description of the disclosure, will be better understood when read in conjunction with the appended drawings. For the purpose of illustrating the disclosure, there is shown in the drawings an embodiment of a fragrance sachet which is presently preferred. It should be understood, however, that the disclosure is not limited to the precise arrangements and instrumentalities shown. In the drawings:

FIG. 4A is a rear elevation view of the fragrance sachet of FIG. 4;

FIG. 5 is a front elevation view of the fragrance sachet of FIG. 4;

DESCRIPTION OF THE DISCLOSURE

Figures 1, 2:
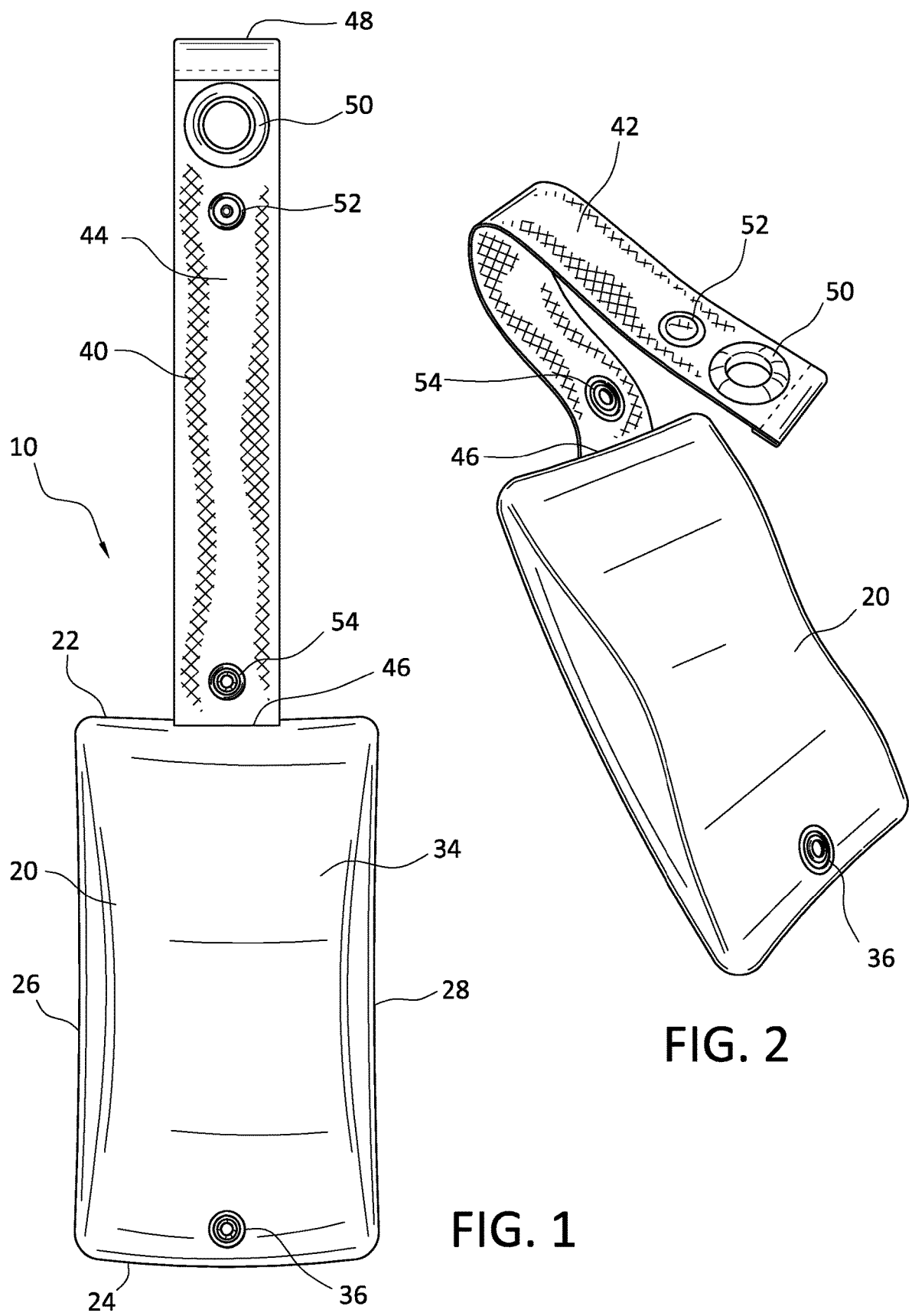
FIG. 1 is a rear elevation view of a fragrance sachet according to the invention.
FIG. 2 is a left rear perspective view of the fragrance sachet of FIG. 1, showing bending of a strap.

Certain terminology is used in the following description for convenience only and is not limiting. The words "lower," "bottom," "upper," "top," "right" and "left" designate directions in the drawings to which reference is made. The words "front", "rear" and "opposite" refer to surfaces in the drawings to which reference is made. Unless specifically set forth herein, the terms "a," "an" and "the" are not limited to one element, but instead should be read as meaning "at least one." The terminology includes the words noted above, derivatives thereof and words of similar import.

It also should be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

As used herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

Referring to the drawings in detail, wherein like numerals indicate like elements throughout, FIG. 1 shows a fragrance sachet 10 configured as a pouch 20 adapted to hold volatile material or filling material impregnated with volatile material or fragrance material. The pouch has a first end 22, an opposite end 24, a left side 26 and a right side 28, a front face 32 and a rear face 34 opposite the front face. The front face 32 may be formed of a same material as the rear face 34, with the two faces 32, 34 sewn or otherwise joined together to form the pouch 20. The front face 32 may be made of a fabric, such as knit, woven or nonwoven, and may be cotton, polyester or a cotton/polyester blend. The rear face 34 may be made of a fabric, such as knit, woven or nonwoven, and may be cotton, polyester or a cotton/polyester blend. At least the front face 32 has a desired air permeability to permit volatile material to be emitted from the pouch 10 and into the air surrounding the pouch 20. Optionally, the rear face 34 of the pouch 40 may be formed of a material impermeable to volatile materials so as to protect mounting surfaces from staining or damage due to contact with the rear face 34 of the pouch 40. For this variant, the rear face 34 may be a polymeric material or a fabric coated with a moisture-resistant coating to deter a volatile material from passing therethrough.

As used herein, "volatile material" refers to a material that is vaporizable. A "volatile material" or a "fragrance material" may be any material that has a smell or odor. Most conventional fragrance materials are highly volatile essential oils. Even those which are less volatile contain highly volatile "top note" fractions which preferably are retained in the composition during processing to obtain desired fragrance power and olfactory impact by the resultant molded article. A fragrance material or a combination of fragrance materials that is compatible with the selected filling material for the pouch is preferred. The fragrance material may be a synthetically formed material or may be a naturally derived oil such as, but not limited to, the oil of Bergamot, Bitter Orange, Caraway, Cedar Leaf, Cedar Wood, Champacc, Cinnamon, Frankincense, Geranium, Lavender, Mimosa, Orange, Orignaum, Patchouli, Rosewood, Sandalwood, Vanilla, Violet, White Cedar, Ylang Ylang, Limonene, menthol, eucalyptus, camphor or the like. The particular essential oil or combination of oils to be used depends upon the fragrance desired for emission by the product formed.

Alternatively or additionally, the fragrance material may comprise or act as a volatile insecticide and/or insecticidal synergist or attractant or repellant, such as pyrethrum, octenol, linalool, mint oil, or a bacteriostat or pheromone. Alternatively or additionally, the fragrance material may comprise or act as a vaporous remedy for respiratory conditions, such as a vapor to relieve symptoms of colds and allergies.

Available fragrance materials are catalogued and described in references and databases known to persons skilled in the art. For example, a database is maintained by the Research Institute for Fragrance Materials at www.rifm.org. Fragrance material suppliers include Takasago International Corp. (Rockleigh, N.J.) and Symrise (Teterboro, N.J.). Exemplary synthetic fragrance materials are described in U.S. Pat. Nos. 4,411,829; 4,314,915 and 4,434,306.

The filling material may be fibers, such as polyester fiber fill or cotton fibers.

The filling material may be flowable particles or mixtures of flowable particles. One exemplary filling material comprises crushed corn cobs having particle sizes with particle diameters from about 1 mm to 3 mm. Crushed buckwheat hulls or other organic hulls also may be used as a filling material. Another exemplary filling material comprises sand, such as silica sand, with grain size from about 0.5 mm to about 4 mm. Yet another exemplary filling material comprises expanded polystyrene (EPS) particles or microbeads with particle diameters from about 1 mm to about 4 mm.

The filling material is impregnated with or coated or wetted with a volatile material/fragrance material. Filling materials with higher porosity pick up a greater amount of volatile material/fragrance material. Filling materials with higher surface area release more of the volatile material to the surrounding air to impart the volatile material to the surrounding air.

A fastener 36 is on or appended to the rear face 34 of the pouch 20. In the embodiment shown in FIGS. 1-8, the fastener 36 is a female snap fastener. It is also contemplated that the fastener 36 may be one tape of a VELCRO® brand hook and loop fastener system.

A strap 40 is joined to the pouch 20. The strap 40 may be formed of a fabric tape, such as a braided or knit fabric tape, having a width of about ¼ inch to 1 inch as desired. The strap may be formed of an elastic band or tape, such as a braided elastic tape having a width of about ¼ inch to 1 inch as desired. As shown in FIGS. 1 and 2, the strap 40 has a front face 42, a rear face 44 that is opposite from the front face, a proximal end 46 and a distal end 48. The strap 40 has a length between its proximal end 46 and its distal end 48. In the embodiment shown in FIGS. 1 and 2, the strap 40 is joined to the pouch 20 at the first end 22 of the pouch 20 with the proximal end 46 of the strap 40 held in the seam holding the front face 32 and the rear face 34 of the pouch together.

Another fastener 54 is on or appended to the rear face 44 of the strap 40. In the embodiment shown in FIGS. 1-8, the fastener 54 is a female snap fastener. If the fastener 36 on the pouch is another type of fastener other than a snap fastener, a complementary fastener that will engage with such other type of fastener is used.

Yet another fastener 52 is on or appended to the rear face 44 of the strap 40. In the embodiment shown in FIGS. 1-8, the fastener 52 is a male snap fastener. The fastener 52 is configured for removable attachment to either the fastener 36 or the fastener 54. If the fasteners 36, 54 are other than snap fasteners, the fastener 52 is a complementary fastener that will engage with either of fasteners 36, 54.

Figures 3, 4:
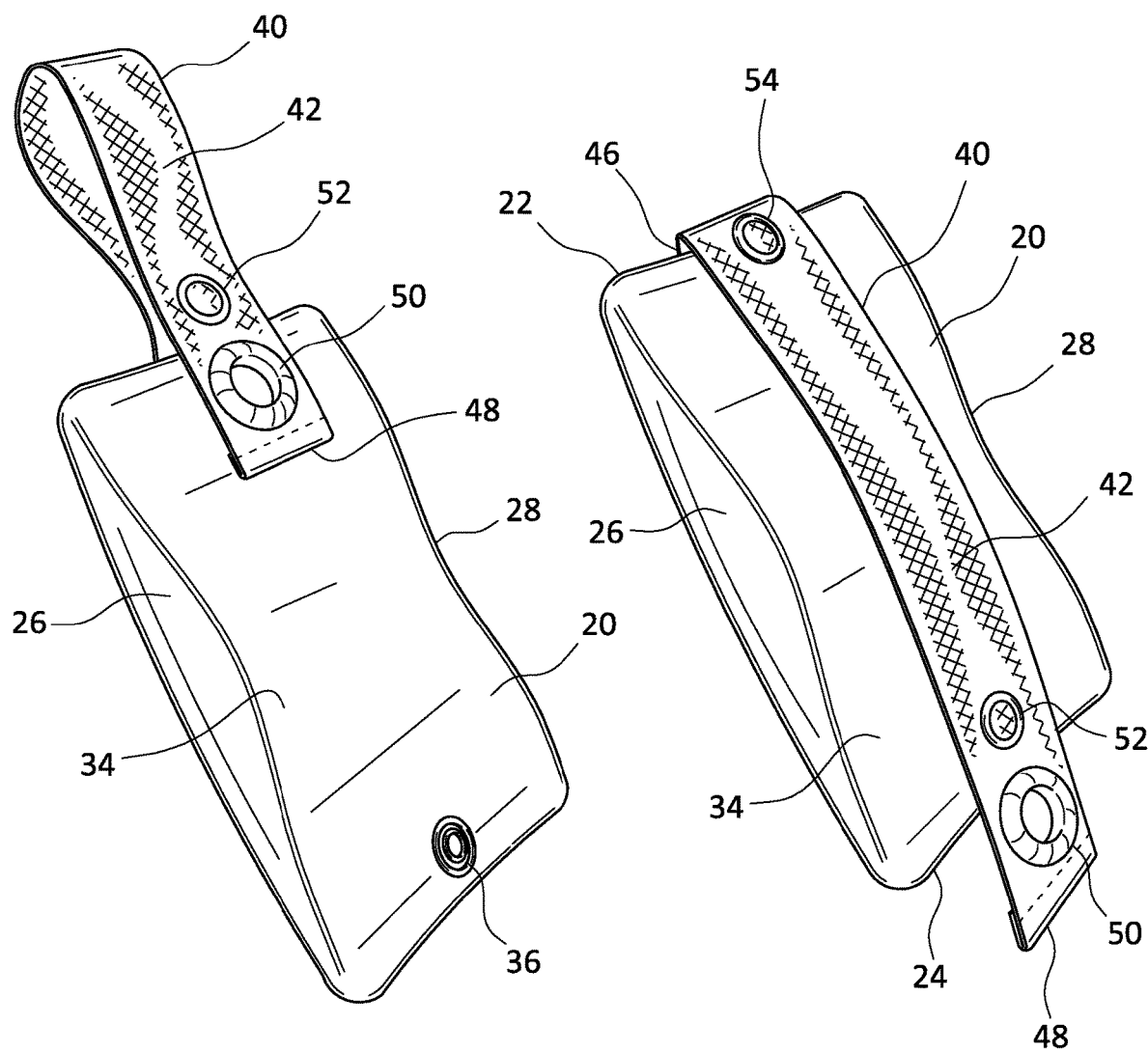
FIG. 3 is a left rear perspective view of the fragrance sachet of FIG. 1, showing the strap forming a loop by connection of snap fasteners on the strap.
FIG. 4 is a left rear perspective view of the fragrance sachet of FIG. 1, showing the strap forming a different loop by connection of a snap fastener on the strap to a snap fastener on the rear face of the fragrance sachet.

Referring to FIGS. 2 and 3, the fastener 52 may be engaged to the fastener 54 so as to form a loop in the strap 40. Referring to FIGS. 2, 4, 4A and 5, the fastener 52 alternatively may be engaged to the fastener 36 so as to form with the strap 40 a handle joined to the rear face 34 of the pouch 20.

In the embodiment shown in the figures, strap 40 defines a hole therethrough that is reinforced by grommet 50 surrounding the hole. The hole and grommet 50 are formed at or near the distal end 48 of the strap 40. As shown in FIG. 1, the fastener 54 is nearest to the proximal end, and the fastener 52 is spaced apart from the fastener 54, and the hole with grommet 50 is spaced farther from the fastener 54. The fasteners 52, 54 and the hole with grommet 50 are oriented with their centers along a center line of the strap 40.

Figure 6:
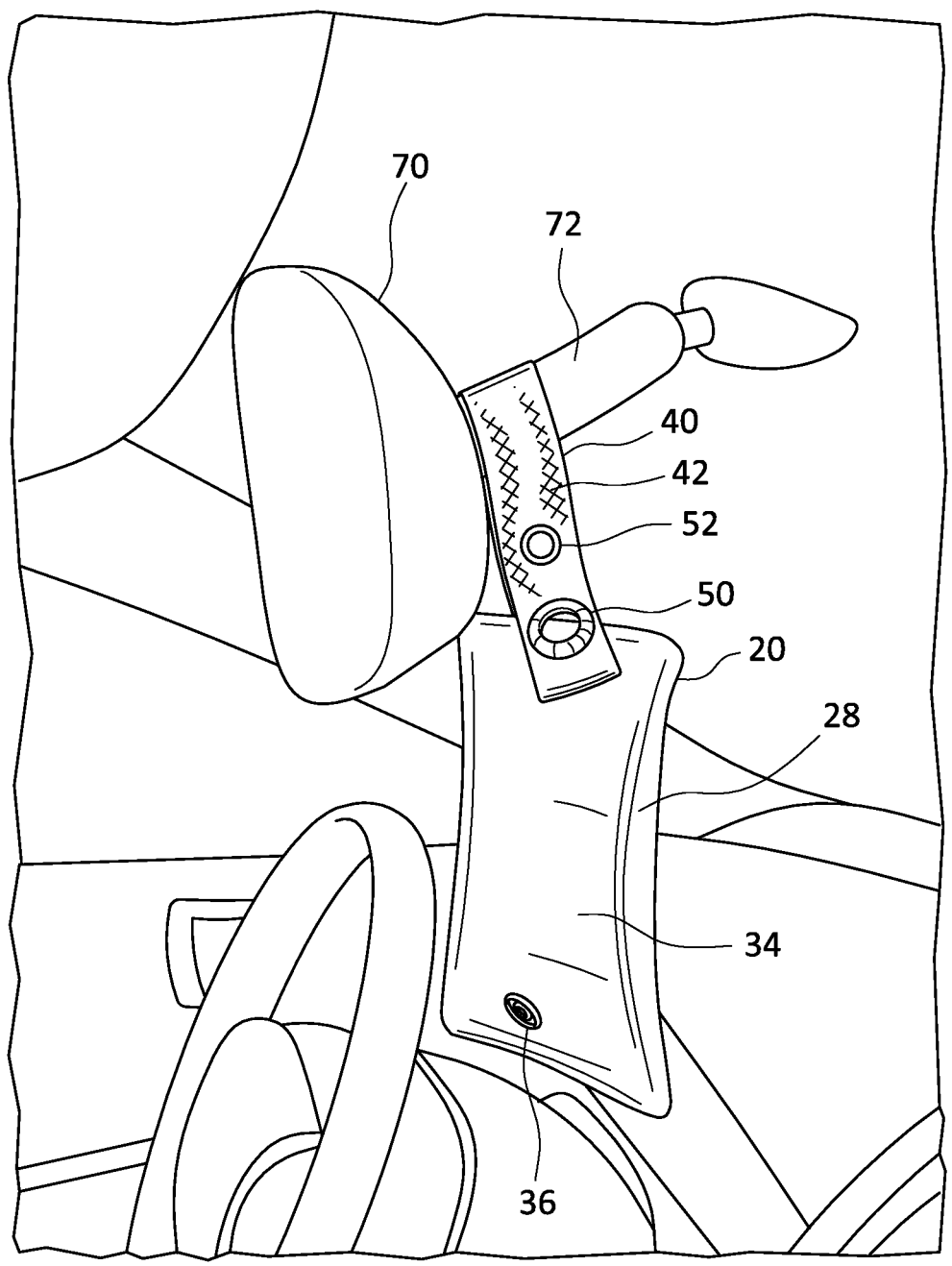
FIG. 6 is a perspective view of the fragrance sachet of FIG. 3 suspended from a neck mount of a rear-view mirror of an automobile.
Figure 7:
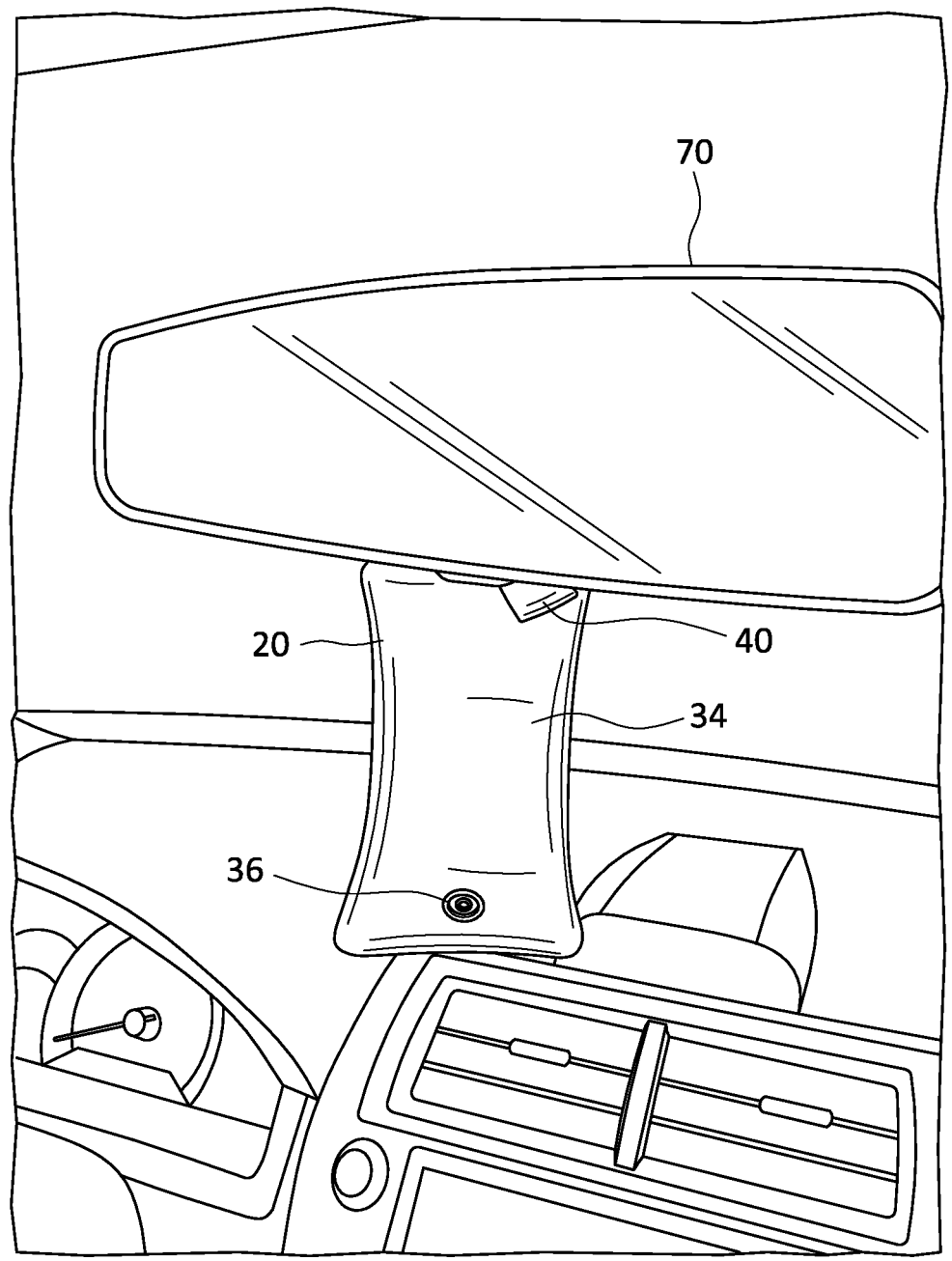
FIG. 7 is a perspective view of the fragrance sachet of FIG. 3 suspended from a neck mount of a rear-view mirror of an automobile.

FIGS. 6 and 7 show the fragrance sachet 10 in a first hanging configuration attached to a neck 72 of a rear-view mirror 70 of a motor vehicle. In the first hanging configuration the strap 40 is formed as a loop with fastener 52 joined to fastener 54, and the pouch 20 suspends from the looped strap 40. In other words, the pouch 20 is hung from the loop formed in the strap 40 (see the fragrance sachet 10 as shown in FIG. 3). The front face 32 of the pouch 20 faces into the vehicle passenger compartment. (Alternatively, the rear face 34 of the pouch 20 could face into the vehicle passenger compartment.) In this first hanging configuration, no portion of the pouch 20 contacts the rear-view mirror 70 or any other surface in the automotive interior. In this manner, the volatile material emitted through the surface(s) of the pouch 20 does not mar or damage the rear-view mirror or any other surface in the automotive interior.

Figure 8:
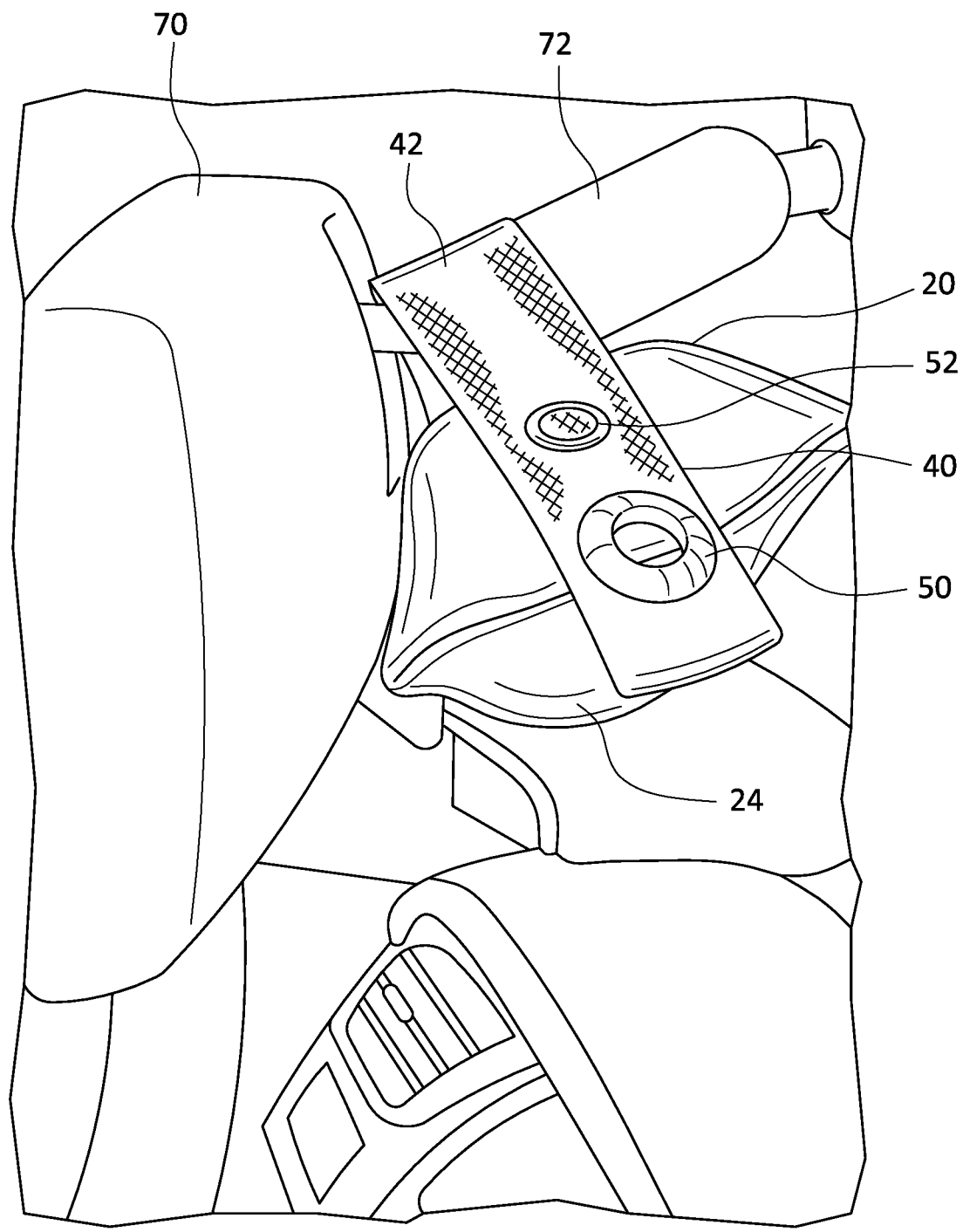
FIG. 8 is a perspective view of the fragrance sachet of FIG. 4 suspended from a neck mount of a rear-view mirror of an automobile.

FIG. 8 shows the fragrance sachet 10 in a second hanging configuration attached to the neck 72 of a rear-view mirror 70. In the second hanging configuration the pouch 20 is suspended from the handle formed by strap 40 when the fastener 52 is joined to the fastener 36 on the rear face 34 of the pouch 20. In other words, the pouch 20 is hung from the strap 40 although there is no "loop" in the strap. The rear face 34 of the pouch 20 faces toward the neck 72 of the rear-view mirror 70, and the front face 32 of the pouch 20 faces downwardly away from the neck 72 of the rear-view mirror 70. (See FIGS. 4, 4A and 5). Preferably, if the rear face 34 will remain in contact with the mounting surface, the rear face 34 of the pouch 20 will be a non-porous material that retards or limits release of volatile material therethrough.

Figure 9:
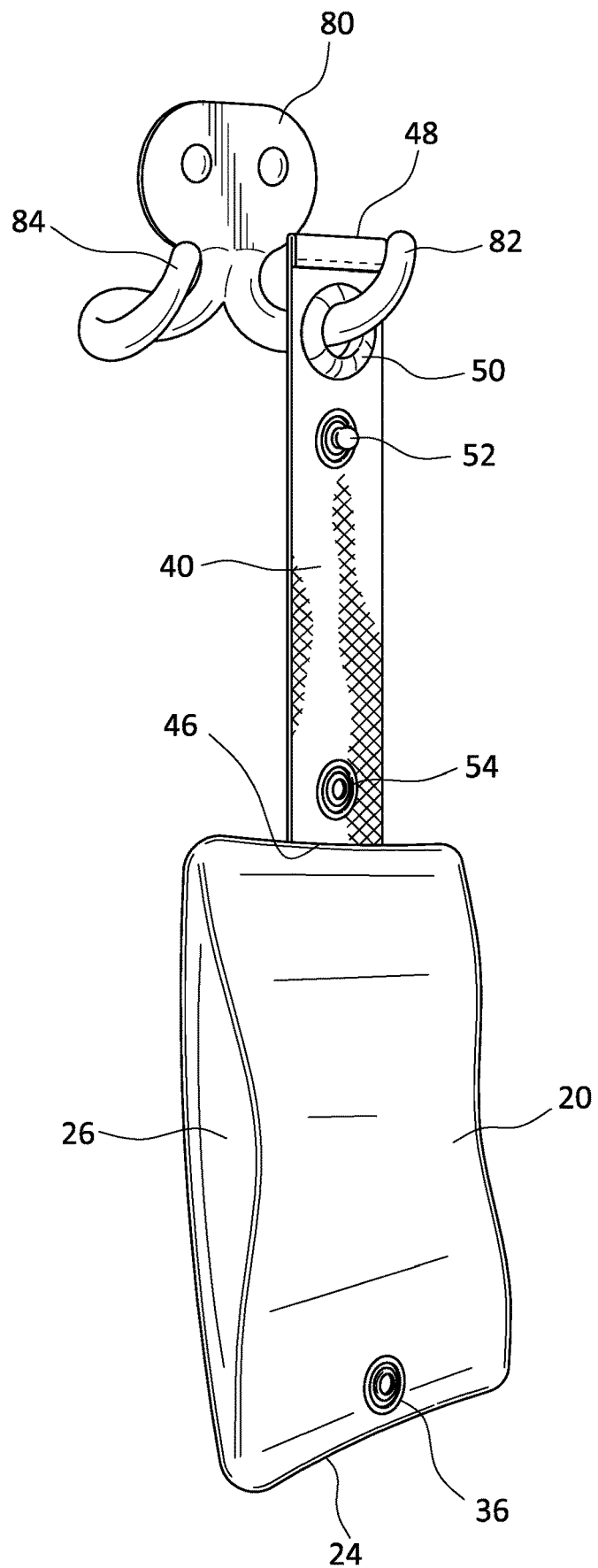
FIG. 9 is a left front perspective view of the fragrance sachet of FIG. 1 hanging by its strap to a coat hook.

FIG. 9 shows the fragrance sachet 10 in a third hanging configuration attached to a coat hook 80. The grommet 50 of the strap 40 is threaded over one arm 82 of the coat hook 80. The coat hook 80 shown has two arms 82, 84. The pouch 20 is suspended by the strap 40 so that no portion of the pouch 20 contacts a furniture surface or closet interior wall. In this manner, the volatile material emitted through the surface(s) of the pouch 20 does not mar or damage the furniture surface or closet interior walls.

If desired, a branded fabric tag 60 may be appended to the pouch 20. If desired, advertising indicia or other artwork design(s) may be added to either the front face 32 or rear face 34 or both faces of the pouch 20, and/or to either the front face 42 or opposite face 44 of the strap 40.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the appended claims.

REFERENCE NUMBERS 10 fragrance sachet
20 pouch
22 first end of pouch
24 opposite end of pouch
26 left side of pouch
28 right side of pouch
32 front face of pouch
34 rear face of pouch 36 female snap fastener
40 strap
42 front face of strap
44 opposite face of strap
46 proximal end of strap
48 distal end of strap
50 grommet
52 male snap fastener
54 female snap fastener
60 branded fabric tag
70 rear view mirror
72 neck of mirror
80 coat hook
82 first hook arm
84 second hook arm

We claim:

1. A method for suspending a fragrance sachet from a support structure, comprising:
   (a) placing a rear face of the fragrance sachet in position adjacent and facing a mounting portion of the support structure, wherein the fragrance sachet has a front face opposite from the rear face, wherein the front face and the rear face are formed of different materials, with the front face of the fragrance sachet formed of a material of an air permeability to permit volatile material(s) to be emitted and with the rear face of the fragrance sachet formed of a material with a lower air permeability than the material forming the front face;
   (b) wrapping a strap joined to the fragrance sachet over the mounting portion of the support structure, wherein said strap has a proximal end and a distal end and a length between the proximal end and the distal end, wherein the proximal end is joined to the fragrance sachet, the strap having a front face and a rear face opposite the front face, and a first fastener positioned at a first location along the length of the strap, and a second fastener positioned at a second location along the length of the strap, spaced apart from the first fastener, and wherein a third fastener is on or appended to the rear face of the fragrance sachet; and
   (c) at a user's option, either (i) securing the second fastener to the third fastener or (ii) securing the second fastener to the first fastener, to suspend the fragrance sachet from the support structure by the strap,
      wherein the front face of the fragrance sachet is free of all fasteners.

2. The method of claim 1, wherein the first fastener and the third fastener each are female snap fasteners, and wherein the second fastener is a male snap fastener.

3. The method of claim 1, wherein at least a portion of the rear face of the pouch remains in contact with the mounting portion of the support structure when the fragrance sachet is suspended from the support structure by the strap.

4. The method of claim 1, wherein only the strap remains in contact with the mounting portion of the support structure when the fragrance sachet is suspended from the support structure by the strap.

5. The method of claim 1, wherein a hole is formed through the strap at a third location along the length of the strap spaced apart from the second fastener, and wherein step (c) further comprises at the user's option (iii) securing the hole onto the mounting structure to suspend the fragrance sachet from the mounting structure by the strap.

6. The method of claim 5, wherein only the strap remains in contact with the mounting portion of the support structure when the fragrance sachet is suspended from the support structure by the hole of the strap.

7. The method of claim 1, wherein the fragrance sachet comprises a pouch configured to receive a volatile material.

8. The method of claim 7, wherein the volatile material comprises a fragrance material selected from the group consisting of: natural and synthetic fragrance oils, and mixtures thereof.

9. The method of claim 7, wherein the pouch is configured to receive a stuffing material that is impregnated with a volatile material.

10. The method of claim 1, wherein the front face of the fragrance sachet is free of all fasteners.

11. The method of claim 1, wherein the rear face of the fragrance sachet is formed of a material impermeable to volatile material(s).

12. The method of claim 1, wherein the support structure comprises structure inside a motor vehicle passenger compartment.

13. The method of claim 1, wherein the support structure comprises structure of or in a closet.

14. The method of claim 1, wherein the support structure comprises an article of furniture.

15. A method for suspending a fragrance sachet from a rearview mirror in a motor vehicle passenger compartment, comprising:
   (a) placing a rear face of the fragrance sachet in position adjacent and facing a mounting portion of the rearview mirror, wherein the fragrance sachet has a front face opposite from the rear face, and wherein the front face and the rear face are formed of different materials, with the front face of the fragrance sachet formed of a material of an air permeability to permit volatile material(s) to be emitted and with the rear face of the fragrance sachet formed of a material with a lower air permeability than the material forming the front face;
   (b) wrapping a strap joined to the fragrance sachet over the mounting portion of the rearview mirror, wherein said strap has a proximal end and a distal end and a length between the proximal end and the distal end, wherein the proximal end is joined to the fragrance sachet, the strap having a front face and a rear face opposite the front face, and a first fastener positioned at a first location along the length of the strap, and a second fastener positioned at a second location along the length of the strap, spaced apart from the first fastener, and wherein a third fastener is on or appended to the rear face of the fragrance sachet, wherein the front face of the fragrance sachet is free of all fasteners; and
   (c) at a user's option, either (i) securing the second fastener to the third fastener or (ii) securing the second fastener to the first fastener, to suspend the fragrance sachet from the rearview mirror by the strap.

* * * * *